United States Patent [19]

Szoka, Jr. et al.

[11] 4,394,149
[45] Jul. 19, 1983

[54] PLANT NUTRIMENT COMPOSITIONS AND METHOD OF THEIR APPLICATION

[76] Inventors: Francis C. Szoka, Jr., 76 Summit St., Waltham, Mass. 02154; Demetrios P. Papahadjopoulos, 3170 Condit St., Lafayette, Calif. 94549

[21] Appl. No.: 149,516

[22] Filed: May 13, 1980

Related U.S. Application Data

[63] Continuation-in-part of Ser. No. 881,116, Feb. 24, 1978, Pat. No. 4,235,871.

[51] Int. Cl.³ ............................................... C05C 9/00
[52] U.S. Cl. ..................................... 71/28; 71/64.11; 71/27; 71/DIG. 2; 424/60; 424/319; 424/365; 427/213.3
[58] Field of Search ................ 71/64 F, 27, 28, 64.11, 71/DIG. 2; 210/500.2; 424/19, 38, 60, 319, 365; 252/316

[56] References Cited

U.S. PATENT DOCUMENTS 3,932,657  1/1976  Rahman ........................... 424/365 X
4,002,458  1/1977  Hofacker ........................ 71/64 F X
4,217,344  8/1980  Vanlerberghe et al. ......... 424/19 X

FOREIGN PATENT DOCUMENTS 48-1137  1/1973  Japan .................................. 71/64 F

OTHER PUBLICATIONS

Lurquin, 1979, Transfer of Plasmid DNA to Protoplasts Arch. Int. Physiol. Biochim. 87(4) 825–826, (Abstract).
Lurquin, 1981, Quamtitative . . . Protoplasts FEBS Lett., 125(2) 183–187 (Abstract).
Lurquin, 1981, Binding . . . Exogenous DNA, Plant Sci. Lett., 21(1) 31–40 (Abstract).
Rollo et al., 1981, Liposome . . . Analysis, Plant Sci. Lett. 20(4), 347–354 (Abstract).

*Primary Examiner*—Ferris H. Lander
*Attorney, Agent, or Firm*—Kane, Dalsimer, Kane, Sullivan & Kurucz

[57] ABSTRACT

The disclosure is of the use of plant nutriments encapsulated in synthetic lipid vesicles to nourish plants.

8 Claims, No Drawings

PLANT NUTRIMENT COMPOSITIONS AND METHOD OF THEIR APPLICATIONSP

CROSS-REFERENCE TO RELATED APPLICATION

This application is a Continuation-in-Part of our copending application Ser. No. 881,116 filed Feb. 24, 1978 and now U.S. Pat. No. 4,235,871.

BACKGROUND OF THE INVENTION

1. Field of the Invention

The invention relates to plant nutriments encapsulated in synthetic lipid vesicles and to their use in agriculture to nourish plants.

2. Brief Description of the Prior Art

Plants, like animals, are nourished by certain nutriments in order to sustain their life. However, unlike animals, plants themselves manufacture the organic nutriments required for assimilation into protoplasmic materials, from more basic elements such as carbon, hydrogen and oxygen. More specifically the plant will itself manufacture the starches and sugars it requires for plant metabolism from carbon, hydrogen and oxygen taken into the plant structure. In addition to carbon, hydrogen, and oxygen, thirteen other elements have been identified as essential to plant nutrition. These are nitrogen and phosphorus (for protein synthesis), potassium calcium, magnesium, sulfur, iron, manganese, copper, zinc, boron, molybdenum, and chlorine. Although the latter elements may be taken into the plant body through the leaf structure, they are more usually taken in by the plant in the form of minerals, dissolved in water and absorbed through the plant's root system from the surrounding soil. These minerals as nutriments may or may not be found in given soils. When they are not, the agriculturist may resort to applying nutriment supplying compositions to the plant situs in the form of fertilizer compositions.

Plant nutrient or nutriment compositions such as commerical fertilizer compositions are of various types. Most of them contain water-disperable or water-soluble materials which can be assimilated by plants. Fertilizers are representative of such nutrient materials. The water-soluble ingredients, such as nitrogen, potassium and phosphorus compounds which are the most commonly used, are often too rapidly leached out of the fertilizer composition are carried away by surface and ground waters long before growing plants can gather and assimilate the nutritive elements. Hence, in many cases a large proportion of desirable nutritive elements is lost and to this extent the fertilizer or other nutrient is wasted.

Numerous attempts have been made in the prior art to reduce water solubility and the leaching rate of fertilizer and like nutrient materials, while at the same time not rendering them incapable of assimilation in growing plants. For example, a number of attempts have been made to incorporate small quantities of fertilizer in fairly high proportions of relatively water-insoluble carriers such as asphalt, resins, plastics, wax and the like; see for example U.S. Pat. Nos. 3,712,867; 3,778,383; and 3,321,298. In some cases the fertilizer ingredients themselves have purposely been made relatively insoluble. In other instances, granules or other small particles of the fertilizer have been coated with water repellent or water resistant materials including such as those named above. In general, these procedures have not been very effective. Thus, if the fertilizer particles are very highly waterproofed, they prevent assimilation by the plants of the needed fertilizer ingredients. If plastic hydrocarbon coating materials which retain a tacky or cold flow property, such as wax or asphalt, are employed, they tend to cohere and agglomerate unduly or to pack in large lumps during periods of storage.

Other difficulties that are encountered in applying fertilizers and like nutrients to soil are (a) neutralization of the materials by reaction with soil components, e.g., phosphate fixation, and (b) their destruction by microorganisms before they can be assimilated by the plant, e.g., the action of denitrifying bacteria.

Basic to the method of our invention is the use of plant nutriments encapsulated in lipid vesicles. When applied to a plant situs the encapsulated nutriments are released slowly at the plant situs over a period of time for absorption by the plant or they may be taken in by the plant in their encapsulated forms. The encapsulated nutriments remain fully bio-available for systemic plant nutrition when absorbed into the plant structure and this unique delivery of nutriments within the plant system may be advantageous in terms of nutritional efficiency.

SUMMARY OF THE INVENTION

The invention comprises a method of nourishing plants, which comprises; applying to the plant situs a nutritional amount of a plant nutriment encapsulated in a lipid vesicle.

The terms "plant nutrient" and "plant nutriment" are interchangeable and as used herein means a nutritious material for plants, i.e.; one which has a nutrient or nourishing effect on the plant.

The term "lipid vesicle" as used throughout the specification and claims means a man-made (synthetic) liposome.

The term "oligolamellar lipid vesicles" as used herein means lipid vesicles as previously defined and characterized in part by few or single bimolecular lipid layers forming the vesicle walls.

The term "plant situs" as used herein means the environmental zone surrounding a given plant, which ordinarily provides nutritional material to the plant.

The method of the invention employs the lipid vesicles containing nutriments for sustained slow release, to effect the growth of plants.

DETAILED DESCRIPTION OF THE PREFERRED EMBODIMENTS OF THE INVENTION

Prior to our invention, several methods were available to make synthetic liposomes, encapsulating biologically active materials; see for example Bangham et al. in J. Mol. Biol., 13:238-252 (1965); D. Papahadjopoulos and N. Miller (Biochim. Biophys. Acta, 135:624-638 [1967]); Batzri and Korn (Biochim. Biophys. Acta, 298:1015 [1973]); Deamer and Bangham in Biochim. Biophys. Acta, 443:629-634 (1976); Papahadjopoulos et al. in Biochim. Biophys. Acta, 394:483-491 (1975); German Pat. No. 2,532,317; and U.S. Pat. Nos. 3,804,776 and 4,016,100.

The prior art methods of making synthetic liposomes may be employed to encapsulate plant nutriments for use in the method of our present invention. However, in a preferred embodiment of our invention the lipid vesicles encapsulating plant nutrients are prepared by our new method of lipid vesicle preparation.

By our new method, oligolamellar lipid vesicles (synthetic liposomes) may be constructed rapidly, conveniently, under mild conditions, in high yields, and in such a manner that they incorporate a high percentage of a wide variety of plant nutriments processed with them. Thus, there is an economic advantage to the encapsulation of plant nutriments by the preferred method.

The preferred method of plant nutriment encapsulation may be carried out by first providing a mixture of a vesicle wall forming compound in organic solvent and an aqueous mixture of the nutrient material to be encapsulated, the ratio of organic phase to aqueous phase being that which will produce an emulsion of the water-in-oil type. One then forms a homogeneous emulsion of said mixture, of the character produced by ultra-sonic radiation. By removing organic solvent from the emulsion, a mixture is obtained having a gel-like character. Then by converting the gel-like mixture to synthetic, oligolamellar vesicles one encapsulates the nutrient material.

The invention also comprises the intermediate gel-like material, the product synthetic lipid vesicles encapsulating nutriments, their use and agriculturally acceptable carrier compositions including the synthetic vesicles as the active ingredient thereof.

In a broad sense, the above-described preferred preparation of the lipid vesicles calls for the formation first of "inverted micelles" in an organic phase and then the removal of the organic phase. The system then spontaneously reverts to a bilayer-like structure, with a large amount of aqueous phase encapsulated in large oligolamellar vesicles. The advantage of this method is that it gives high capture efficiencies of nutriment containing aqueous phase and provides large, stable vesicles. Phospholipids are excellent molecules for the formation of the "inverted micelles" and then the subsequent bilayer of the vesicles. More specifically, the method of the lipid vesicle preparation may be carried out as follows.

The first step is to provide a mixture of a lipid vesicle wall forming composition in organic solvent and an aqueous mixture of the plant nutriment to be encapsulated in the vesicle. Vesicle wall forming compounds are generally well known as are the methods of their preparation. For example, any number of phospholipids or lipid compounds may be used to form the vesicle walls. Representative of such wall forming compounds are: phosphatidylcholine (hereinafter referred to as "PC"), both naturally occurring and synthetically prepared, phosphatidic acid (hereinafter referred to as "PA"), lysophosphatidylcholine, phosphatidylserine (hereinafter referred to as "PS"), phosphatidylethanolamine (hereinafter referred to as "PE"), sphingolipids, phosphatidyglycerol (hereinafter referred to as "PG"), spingomyelin, cardiolipin, glycolipids, gangliosides, cerebrosides and the like used either singularly or intermixed such as in soybean phospholipids (Asolectin, Associated Concentrates). In addition, other lipids such as steroids, cholesterol, aliphatic amines such as long chain aliphatic amines and carboxylic acids, long chain sulfates and phosphates, dicetyl phosphate, butylated hydroxytoluene, tocophenol, retinol, and isoprenoid compounds may be intermixed with the phospholipid components to confer certain desired and known properties on the formed vesicles. In addition, synthetic phospholipids containing either altered aliphatic portions such as hydroxyl groups, branched carbon chains, cycloderivatives, aromatic derivatives, ethers amides, polyunsaturated derivatives, halogenated derivatives or altered hydrophillic portions containing carbohydrate, glycol, phosphate, phosphonate, quaternary amine, sulfate sulfonate, carboxy, amine, sulfhydryl, imidazole groups and combinations of such groups can be either substituted or intermixed with the above mentioned phospholipids and used in the preferred process of lipid vesicle formation. It will be appreciated from the above that the chemical composition of the lipid component of the vesicles prepared may be varied greatly without appreciable diminution of percentage nutriment capture although the size of the vesicle may be affected by the lipid composition. A convenient mixture we have used extensively and which is representative of lipid mixtures advantageously used in preferred lipid vesicle preparation is composed of PS and PC, or PG and PC as identified above (advantageously at a 1:4 molar ratio in each instance). The PC, PG, PA and PE, may be derived from purified egg yolk. Saturated synthetic PC and PG, such as dipalmitoyl may also be used. Other amphipathic lipids that may be used, advantageously in various mixtures, are gangliosides, globosides, fatty acids, stearylamine, long chain alcohols, long chain sulfates and the like.

The liposome wall forming composition may be initially provided dissolved in any inert solvent that can be substantially removed from the lipid or phospholipid compound when desired. Representative of such solvents are a wide variety of ethers, esters, alcohols, ketones, hydrocarbons (aromatic and aliphatic including fluorocarbons), and silicones in which an aqueous phase does not have an appreciable solubility. The solvents may be used either alone or in admixture. For each solvent or mixture of solvents however, the optimal ratio of lipid, aqueous space, and solvent is different and must be determined for each case by trial and error techniques as will be appreciated by those skilled in the art. The term "inert solvent" as used herein means a solvent for the lipid or phospholipid, which will not interfere with or otherwise adversely affect the desired course of the preferred preparative method.

The phospholipid or lipid along with any lipid-soluble additives, are advantageously evaporated from their solvent on to the sides of a suitable reaction vessel. The organic phase, in which the "reversed phase evaporation vesicles" will be formed is then added to the vessel, i.e.; an inert organic solvent for the lipids and phospholipids as described above. With mixing, dissolution of the lipid component of the vesicles to be formed, previously deposited on the vessel walls is obtained. A number of inert organic solvents are preferred for forming the organic phase according to the preferred preparative method, depending on the following conditions employed. For low temperature conditions, i.e.; removal subsequently of the organic phase at relatively low temperatures, we find diethyl ether most advantageous, although chloroform, or tetrahydrofuran may also be used advantageously. For higher temperature processing, isopropyl ether is a preferred inert organic solvent, particularly for preparing lipid vesicles containing saturated phospholipids as the lipid component. Following dissolution of the phospholipid or lipid to form the organic phase, an aqueous phase is added to obtain a heterogeneous 2-phase mixture. The aqueous phase contains in dissolution/suspension the nutriment compounds or compositions to be encapsulated in the synthetic lipid vesicles produced by the preferred preparative method. Preferably the aqueous phase is buffered to a pH suitable to maintain stability of the material for encapsulation. The ionic strength of the aqueous phase has a bearing on the encapsulation efficiency obtained in the preferred preparative method. As a general rule, the higher the ionic strength of the aqueous phase, the lower the percentage of entrapment. For example, with 15 mM sodium chloride present, one can encapsulate circa 60 percent of the aqueous phase, while with 500 mM sodium chloride present, only about 20 percent of the aqueous phase may be encapsulated. Thus, to maximize the encapsulation of macromolecules, a buffer of low ionic strength (less than 0.3) is preferably employed. The encapsulation efficiency is also dependent to some degree on the concentration of lipid or phospholipid present in the 2-phase system. Preferably the proportion of lipid or phospholipid component is within the range of from about 0.5 mg to about 50 mg/ml. of the inert organic solvent. Preferably the ratio of organic phase to aqueous phase is within the range of from about 2:1 to about 20:1 v/v, most preferably about 4:1 to form a water-in-oil emulsion.

The heterogeneous 2-phase mixture obtained as described above is then emulsified to obtain an emulsion of the character produced by ultrasonic radiation. Preferably this is accomplished with the use of a bath type sonicator, or for large volume preparations in an industrial size emulsifier. Generally, the 2-phase mixture is sonicated for about 3 to 5 minutes, or until either a clear 1-phase mixture or a homogeneous emulsion forms. This is achieved by simply placing the container vessel in the sonicating bath at an optimal level. Emulsification may be carried out over a wide range of temperatures, i.e.; from about $-10°$ to about $50°$ C., advantageously at a temperature of from $0°-20°$ C. The optimum conditions under which emulsification is carried out depends upon the solvent, phospholipid, and volume of aqueous phase used in the preparation. It will be appreciated that trial and error techniques may be used to determine the optimum conditions for emulsification. The emulsion mixture is then treated to remove a substantial portion of the inert organic solvent. This may be carried out conveniently by use of a rotary evaporator, at a temperature of circa $20°$ C. to $60°$ C. and under a reduced pressure, i.e.; under vacuum (10 mm to 50 mm Hg). The temperature employed for evaporation of the organic solvent from the emulsion depends on the boiling point of the particular organic solvent used in the emulsion and the stability of the nutriment material being encapsulated. During evaporation, the emulsion first becomes a viscous gel, which is an intermediate product. The gel is stable and can be stored in this state for short periods of time, up to a week (at least), at $4°$ C. under an inert atmosphere such as nitrogen gas. A small amount of water or buffer can then be added to the gel and the resulting mixture evaporated for an additional period (circa 15 minutes) to help remove residual traces of the organic solvent, and to speed the conversion of the gel into a homogeneous-appearing, suspension of oligolamellar lipid vesicles. The gel may be converted by agitation or by dispersion in an aqueous media such as a buffer solution. The vesicles obtained range in diameter from 2,000 to 4,000 angstroms (average). A significant proportion of the nutriment compounds for encapsulation contained in the aqueous buffer is captured within the lipid vesicles (up to circa 60 percent, depending on the amount of lipid, volume of the aqueous phase, ratio of the organic phase to aqueous phase to lipid, type of inert organic solvent(s) and, type of lipid(s) used in the process). The non-incorporated aqueous material may be removed if necessary by appropriate and known techniques such as by repeated centrifugations, column chromatography, ion exchange chromatography, dialysis and like procedures. Generally however separation is not necessary and the crude mixture may be used as is in the method of the invention. The lipid vesicles with their encapsulated contents may be suspended in any isotonic buffer for use. The vesicles may be sterilized by passage through a 0.4 micron filter (nucleopore) when sterility is desired.

Advantageously the preferred method of preparing nutrient containing lipid vesicles is carried out under an inert atmosphere. The term "inert atmosphere" as used herein means a non-oxidizing atmosphere such as an atmosphere of nitrogen gas, argon and like inert gases.

Representative of nutriment materials that may be encapsulated by the method described above are vitamins, minerals, growth stimulating hormones, growth promoters such as diallyl pimelate, the auxins such as 3-indoleacetic acid, 3-indolebutyric acid and the like, the gibberellins such as gibberellic acid ($GA_3$) and the like; fertilizers such as urea, calcium cyanamide, ammonium nitrate, ammonium sulfate, sodium nitrate, calcium nitrate, ammonium phosphate, potassium nitrate, potassium chloride, mixtures thereof (multinutrient fertilizers) and the like. The encapsulated nutriments cannot be readily removed from the area site of application (plant situs) by rain or irrigation. Encapsulation of the nutrient materials protects them from inactivation or removal, i.e.; maintains plant bioavailability for agricultural crops to which the encapsulated material is applied according to the method of our invention.

It will be observed from the above that our preferred method of preparing nutrient containing lipid vesicles differs from the prior art methods, of making vesicles in several ways. For example, according to our preferred method the nutrient material to be encapsulated is added into the organic phase with the lipid where it is totally encapsulated. Furthermore, the organic phase is substantially removed before an excess of an aqueous phase is added. The emulsification of the initial aqueous phase into the organic phase, and the removal of the organic phase prior to the addition of any excess aqueous phase is essential for high capture percentage in this method and is a critical difference between our preferred process and all previous methods heretofore described for lipid vesicle preparation. The method we advocate produces large oligolamellar vesicles from many different lipids either alone or in combinations. A further advantage is that the evaporation of the organic phase is performed under mild temperatures and vacuum to obviate the potential for inactivation of sensitive nutrient molecules.

The method of the invention is carried out by applying to a plant situs, a nutritional amount of a plant nutrient encapsulated in a lipid vesicle. Application may be to the plant leaves, but is preferably to the surrounding soil. The amount which constitutes a nutritional amount will vary depending on the plant, plant nutritional needs, etc.

The question in most instances is how much fertilizer to use on a soil that is not at an optimum level of fertility. Soil tests can be made by which the amount of available nutrients in the soil can be determined. The amounts needed for various plants and crops are generally known. From experience it can then be predicted how much fertilizer or nutriment should be applied to a given situs, i.e.; the rate of nutriment application. Those skilled in the art of agriculture will appreciate how to determine rates of nutriment application.

The lipid vesicle encapsulated nutriment compositions may be applied to a given plant situs in a dispersible pure form, i.e.; as obtained directly by the above-described method of encapsulation but dispersible agricultural formulations for fertilizer uses are preferred. The dispersible agricultural formulations of this invention comprise a lipid vesicle encapsulated nutriment in a homogeneous, dispersible form with a homogeneous, dispersible, agriculturally acceptable carrier. A homogeneous, dispersible, agriculturally acceptable carrier preferably comprehends a liquid carrier diluent. The lipid vesicles can be dispersed in a liquid carrier diluent as finely divided particles (suspension).

The term "dispersible", as used in this specification and in the claims, means matter dispersed in a liquid such that it can be evenly distributed over a given area or situs. Emulsions and suspensions of lipid vesicles in water are one embodiment of dispersible formulation contemplated.

In addition to containing the nutriment encapsulated lipid vesicles, the dispersible carrier formulations of the invention may include a variety of adjuvants such as humecants, dispersants, adhesive or sticking agents, corrosion inhibitors, and anti-foaming agents. Illustrative of such adjuvants are humecants such as glycerol, diethylene glycol. solubilized lignins (such as calcium ligninsulfonate) and the like. Dispersants include methyl cellulose, polyvinyl alcohol, sodium ligninsulfonate and the like. Adhesive or sticking agents include vegetable oils, naturally occurring gums, casein, and the like. A representative corrosion inhibitor is epichlorohydrin, and a representative anti-foaming agent is stearic acid. The concentration of the active ingredient, i.e.; the lipid vesicles present in the agriculturally acceptable carrier is not critical and any concentration desired may be used. As a practical matter, from 10 to 80 percent by weight lipid vesicles in the carrier are advantageous concentrations.

The most important factor is how much nutriment is applied to a given plant situs. It is readily apparent that one can apply a large amount of a formulation having a low concentration of nutriment or a relatively small amount of a formulation having a high concentration. Whether a low or high concentration should be used depends upon the mode of application, the amount and kinds of vegetation, and the thoroughness of coverage desired. The total amount to be applied depends upon the kinds of crop, the severity of nutritional need, the state of plant development, and the season of the year as those skilled in the art will appreciate and as discussed above.

Representative homogeneous dispersible formulations according to this invention include sprays and delivery by irrigation means such as canals, etc. Spray formulations are preferred for foliar applications and for uniformly controlled applications to a soil. The spray formulations in accordance with the invention may be aqueous suspensions, oil-in-water emulsions and the like. The lipid vesicles may also be dispersed in a suitable water-miscible inert organic liquid. Representative of water-miscible, inert organic liquids are acetone, methyl ethyl ketone, dimethylformamide, alcohols, monoalkyl ethers of ethylene glycol, ethyl acetate, and the like. The spray formulations will conveniently comprise from about 0.1% or lower to about 50% by weight or even higher, a volume of spray being applied so that a nutritionally effective amount of nutriment is applied to a given situs.

The following examples describe the manner and process of making and using the invention and represent the best mode contemplated by the inventors, but are not to be construed as limiting. In all of the procedures described below, one can include 0.5 to 1 mole of a fluorescent phospholipid analog such as NBD-PE (Avanti Biochemicals) with the lipid or phospholipid component in order to be able to visually follow the separation of the vesicles on a column.

EXAMPLE 1

Encapsulation of Urea

A 50 ml round bottom flask with a long extension neck is fitted with a 24/40 fitting so as to conveniently couple to a flask evaporator. The flask is also fitted for continuous purging with nitrogen gas. The flask is charged with $300\mu$ moles of phospholipid-phosphatidylglycerol/phosphatidylcholine/cholesterol (PG/PC/Chol) 1/4/5 molar ratio in 15 ml diethylether and 5 ml of a solution of 8 M urea in water is added. The mixture is emulsified by ultrasonic treatment. The organic solvent is then removed by evaporation. The preparation so formed contains a mixture of 50% encapsulated urea and 50% non-encapsulated urea that can be applied to agricultural crops as a slow release fertilizer. Application may be by spray technique. The encapsulated urea is protected from washout by rain or irrigation and from degradation by urease enzymatic activity in the soil. The lipid vesicles are also wholly absorbed by the plant through its root structure and deliver the nutriment urea at the cellular level.

EXAMPLE 2

Encapsulation of Micronutrients in Vesicles as a Slow Release Fertilizer to Treat Plants Afflicted by Iron Chlorosis Five ml of a solution containing 1% ferrous ethylene diamine tetraacetic acid complex (EDTA) 1% zinc EDTA is added to the flask described in Example 1, containing 15 ml of diethylether containing $300\mu$ moles of PG/PC/Chol:1/4/5. Vesicles are prepared as described in Example 1 above. The unencapsulated Fe-EDTA, and ZnEDTA are removed by dialysis and the FeEDTA and ZN-EDTA that remains encapsulated may be spray applied to agricultural plants as a slow release micronutrient reservoir to treat chlorosis in affected plants.

By changing the lipid composition from PG/PC/Chol to DSPC (distearoylphosphatidylchloine) and encapsulating the above compounds the rate of release of the fertilizer will be appreciably slowed when compared to the PG/PC/Chol composition. Thus, by using phospholipids with different characteristic transition temperatures, one can prepare liposomes that will have defined permeability rates. The shorter the acyl chains and the greater the degree of unsaturation of the phospholipids used to prepare the vesicles the faster the rate of leakage of the nutrients from the vesicles. The lipid vesicles are taken into the plant system through the root structure and assimilated within the plant, at the cellular level.

What is claimed is:

1. A method of providing nutriments to agricultural plants possessing plant cells having cell walls and cell membranes, which comprises; applying to the plant a nutritional amount of a plant nutriment, encapsulated in a lipid vesicle, whereby the lipid vesicle encapsulating the plant nutriment is taken up by the plant and passes into the plant cell where the lipid vesicle is broken down and releases the encapsulated plant nutriment.

2. The method of claim 1 wherein the lipid vesicles are in a dispersible form with a dispersible agriculturally acceptable carrier.

3. The method of claim 1 wherein said applying is by spray.

4. The method of claim 1 wherein the nutriment is urea.

5. The method of claim 1 wherein the nutriment comprises ferrous ethylenediamine tetraacetic acid complex and zinc ethylenediamine tetraacetic acid complex.

6. The method of claim 1 wherein the nutriment is a fertilizer.

7. The method of claim 1 wherein the lipid vesicles have an average diameter of from 2000 to 4000 angstroms.

8. The method of claim 7 wherein the lipid vesicles are oligolamellar lipid vesicles.

* * * * *